(12) United States Patent
Germeyer et al.

(10) Patent No.: US 7,429,600 B2
(45) Date of Patent: *Sep. 30, 2008

(54) FLUORENECARBOXYLIC ACID ESTERS, PROCESS FOR THE MANUFACTURE THEREOF, AND USE THEREOF AS MEDICAMENTS

(75) Inventors: Sabine Germeyer, Biberach an der Riss (DE); Helmut Meissner, Ingelheim (DE); Gerd Morschhauser, Biberach (DE); Sabine Pestel, Biberach (DE); Michael P. Pieper, Biberach (DE); Gerald Pohl, Biberach (DE); Richard Reichl, Gau-Algesheim (DE); Georg Speck, Ingelheim am Rhein (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/558,718

(22) Filed: Nov. 10, 2006

(65) Prior Publication Data

US 2007/0086951 A1   Apr. 19, 2007

Related U.S. Application Data

(63) Continuation of application No. 11/254,311, filed on Oct. 20, 2005, now Pat. No. 7,214,797, which is a continuation of application No. 10/914,744, filed on Aug. 9, 2004, now Pat. No. 6,998,406, which is a continuation of application No. 10/772,797, filed on Feb. 5, 2004, now Pat. No. 6,815,452, which is a continuation of application No. 10/335,795, filed on Jan. 2, 2003, now Pat. No. 6,790,856.

(60) Provisional application No. 60/368,416, filed on Mar. 28, 2002.

(30) Foreign Application Priority Data

Jan. 31, 2002 (DE) ................. 102 03 741

(51) Int. Cl.
  A61K 31/46 (2006.01)
  C07D 491/08 (2006.01)
  C07D 451/02 (2006.01)
(52) U.S. Cl. .................. 514/291; 546/91; 546/128; 514/304
(58) Field of Classification Search ............ 514/291, 514/304; 546/91, 128
See application file for complete search history.

(56) References Cited

U.S. PATENT DOCUMENTS

| 4,042,700 | A | 8/1977 | Banholzer et al. |
| 4,608,377 | A | 8/1986 | Banholzer et al. |
| 4,783,534 | A | 11/1988 | Banholzer et al. |
| 5,610,163 | A | 3/1997 | Banholzer et al. |
| 5,654,314 | A | 8/1997 | Banholzer et al. |
| 5,770,738 | A | 6/1998 | Banholzer et al. |
| 5,952,505 | A | 9/1999 | Banholzer et al. |
| 6,486,321 | B2 | 11/2002 | Banholzer et al. |
| 6,506,900 | B1 | 1/2003 | Banholzer et al. |
| 6,790,856 | B2 | 9/2004 | Germeyer et al. |
| 6,815,452 | B2* | 11/2004 | Germeyer et al. ........... 514/304 |
| 6,998,406 | B2* | 2/2006 | Germeyer et al. ........... 514/291 |
| 7,214,797 | B2* | 5/2007 | Germeyer et al. ............. 546/91 |
| 2002/0115680 | A1 | 8/2002 | Meissner et al. |
| 2002/0119991 | A1 | 8/2002 | Meissner et al. |
| 2003/0199539 | A1 | 10/2003 | Germeyer et al. |
| 2003/0203928 | A1 | 10/2003 | Germeyer et al. |
| 2003/0207912 | A1 | 11/2003 | Eickmeier et al. |

FOREIGN PATENT DOCUMENTS

WO   WO 92/16528   10/1992

OTHER PUBLICATIONS

Safrazbekyan, R. R. et al.: Effect of atropine analogs on experimental bronchial spasm. Izvestiya Nauk Armyanskoi SSR, Biologicheskie Nauki, vol. 16, pp. 7-13, 1963.*

Bowden, Keith et al; Structure-activity relations. I. Series of antagonists of acetylcholine and histamine at the postganglionic receptors, Journal of Medicinal Chemistry (1970), 13(2), 225-30, XP000960623.

Stubbins, James F. et al ; Muscarinic M1 and M2 binding affinity of cyclic amine derivatives of caramiphen and dicyclomine; Medicinal Chemistry Research (1992), 2(6), 384-93 XP009011390.

Albanus, Lennart; Central and peripheral effects of anticholinergic compounds; ACTA Pharmacologica et Toxicologica (1970), 28(4), 305-26, XP009011388.

Farquharson, Muriel, et al; Antagonism of the effects of tremorine by tropine derivatives, Brit. J. Pharmacol. (1959), 14, 559-66, XP009011410.

Meyerhoffer, Anita et al; Acid-base properties of atropine, scopolamine and some glycolic acid esters; ACTA Chemica Scandinavica (1947-1973), (1973), 27(3), 868-74, XP009011391.

* cited by examiner

*Primary Examiner*—Charanjit S Aulakh
(74) *Attorney, Agent, or Firm*—Michael P. Morris; Mary-Ellen M. Devlin; Wendy A. Petka

(57) ABSTRACT

Fluorenecarboxylic acid esters of general formula 1

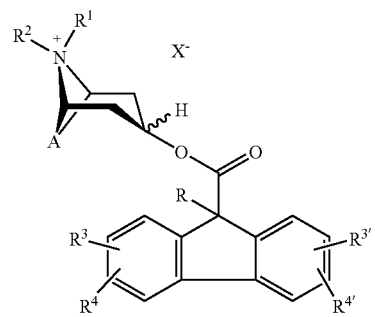

wherein $X^-$ and the groups A, R, $R^1$, $R^2$, $R^3$, $R^{3'}$, $R^4$, and $R^{4'}$ have the meanings given in the claims and in the specification, processes for the manufacture thereof and the use thereof as medicaments.

20 Claims, No Drawings

FLUORENECARBOXYLIC ACID ESTERS, PROCESS FOR THE MANUFACTURE THEREOF, AND USE THEREOF AS MEDICAMENTS

SUMMARY OF THE INVENTION

The present invention relates to new fluorenecarboxylic acid esters of general formula 1

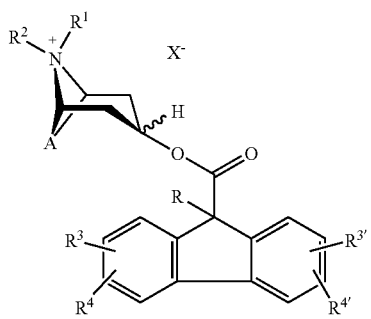

wherein $X^-$ and the groups A, R, $R^1$, $R^2$, $R^3$, $R^{3'}$, $R^4$, and $R^{4'}$ may have the meanings given in the claims and in the description, processes for preparing them and their use as pharmaceutical compositions.

BRIEF DESCRIPTION OF THE INVENTION

The present invention relates to compounds of general formula 1

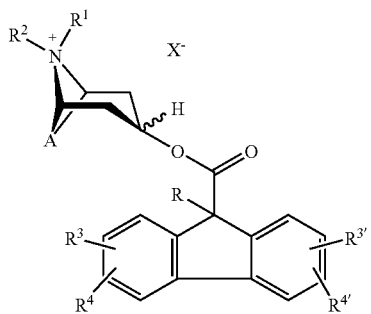

wherein:

A denotes a double-bonded group selected from among

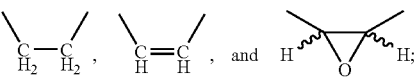

$X^-$ is an anion with a single negative charge, preferably an anion selected from among chloride, bromide, iodide, sulfate, phosphate, methanesulfonate, nitrate, maleate, acetate, citrate, fumarate, tartrate, oxalate, succinate, benzoate, and p-toluenesulfonate;

R denotes hydrogen, hydroxy, methyl, ethyl, —$CF_3$, —$CHF_2$, or fluorine;

$R^1$ and $R^2$, which may be identical or different, denote $C_1$-$C_5$-alkyl which may optionally be substituted by $C_3$-$C_6$-cycloalkyl, hydroxy, or halogen, or $R^1$ and $R^2$ together denote a —$C_3$-$C_5$-alkylene-bridge; and $R^3$, $R^4$, $R^{3'}$, and $R^{4'}$, which may be identical or different, denote hydrogen, —$C_1$-$C_4$-alkyl, —$C_1$-$C_4$-alkyloxy, hydroxy, —$CF_3$, —$CHF_2$, —CN, —$NO_2$, or halogen.

Preferred compounds of general formula 1 are those wherein

A denotes a double-bonded group selected from among

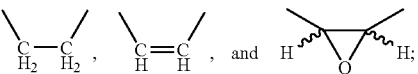

$X^-$ denotes an anion with a single negative charge selected from among chloride, bromide, 4-toluenesulfonate, and methanesulfonate, preferably bromide;

R denotes hydroxy, methyl, or fluorine;

$R^1$ and $R^2$, which may be identical or different, denote methyl, ethyl, or fluoroethyl;

$R^3$, $R^4$, $R^{3'}$, and $R^{4'}$, which may be identical or different, represent hydrogen, methyl, methyloxy, hydroxy, —$CF_3$, —$CHF_2$, or fluorine.

Particularly preferred compounds of general formula 1 are those wherein

A denotes a double-bonded group selected from among

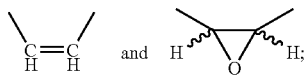

$X^-$ denotes an anion with a single negative charge selected from among chloride, bromide, and methanesulfonate, preferably bromide;

R denotes hydroxy, methyl, or fluorine, preferably methyl or hydroxy;

$R^1$ and $R^2$, which may be identical or different, represent methyl or ethyl, preferably methyl;

$R^3$, $R^4$, $R^{3'}$ and $R^{4'}$, which may be identical or different, represent hydrogen, —$CF_3$, —$CHF_2$, or fluorine, preferably hydrogen or fluorine.

Of particular importance according to the invention are compounds of general formula 1 wherein:

A denotes a double-bonded group selected from among

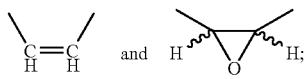

X⁻ denotes bromide;

R denotes hydroxy or methyl, preferably methyl;

$R^1$ and $R^2$, which may be identical or different, represent methyl or ethyl, preferably methyl; and $R^3$, $R^4$, $R^{3'}$, and $R^{4'}$, which may be identical or different, represent hydrogen or fluorine.

The invention relates to the compounds of formula 1 optionally in the form of the individual optical isomers, mixtures of the individual enantiomers, or racemates.

In the compounds of general formula 1 the groups $R^3$, $R^4$, $R^{3'}$, and $R^{4'}$, if they do not represent hydrogen, may in each case be arranged in the ortho, meta or para position relative to the bond to the "—C—R" group. If none of the groups $R^3$, $R^4$, $R^{3'}$, and $R^{4'}$ denotes hydrogen, $R^3$ and $R^{3'}$ are preferably linked in the para position and $R^4$ and $R^{4'}$ are preferably linked in the ortho or meta position, most preferably in the meta position. If one of the groups $R^3$ and $R^4$ and one of the groups $R^{3'}$ and $R^{4'}$ denotes hydrogen, the other group in each case is preferably bonded in the meta or para position, most preferably in the para position. If none of the groups $R^3$, $R^4$, $R^{3'}$, and $R^{4'}$ denotes hydrogen, the compounds of general formula 1 wherein the groups $R^3$, $R^4$, $R^{3'}$, and $R^{4'}$ have the same meaning are particularly preferred according to the invention.

Also of particular importance according to the invention are those compounds of general formula 1 wherein the ester substituent is in the α configuration on the nitrogen bicyclic group. These compounds correspond to general formula 1-α

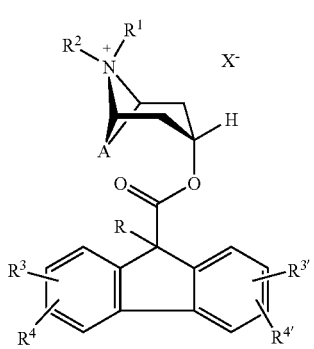

1-α

The following compounds are of particular importance according to the invention: tropenol 9-hydroxyfluorene-9-carboxylate methobromide; tropenol 9-fluorofluorene-9-carboxylate methobromide; scopine 9-hydroxyfluorene-9-carboxylate methobromide; scopine 9-fluorofluorene-9-carboxylate methobromide; tropenol 9-methylfluorene-9-carboxylate methobromide; and scopine 9-methylfluorene-9-carboxylate methobromide.

The alkyl groups used, unless otherwise stated, are branched and unbranched alkyl groups having 1 to 5 carbon atoms. Examples include: methyl, ethyl, propyl, or butyl. The groups methyl, ethyl, propyl, or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and isopropyl, butyl includes isobutyl, sec-butyl, and tert-butyl, etc.

The alkylene groups used, unless otherwise stated, are branched and unbranched double-bonded alkyl bridges with 1 to 4 carbon atoms. Examples include: methylene, ethylene, propylene, or butylene.

The alkylene-halogen groups used, unless otherwise stated, are branched and unbranched double-bonded alkyl bridges with 1 to 4 carbon atoms which may be mono-, di-, or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di-, or trisubstituted, preferably monosubstituted, by a hydroxy.

The alkyloxy groups used, unless otherwise stated, are branched and unbranched alkyl groups with 1 to 4 carbon atoms which are linked via an oxygen atom. The following may be mentioned, for example: methyloxy, ethyloxy, propyloxy, or butyloxy. The groups methyloxy, ethyloxy, propyloxy, or butyloxy may optionally also be referred to by the abbreviations MeO, EtO, PropO, or BuO. Unless otherwise stated, the definitions propyloxy and butyloxy also include all possible isomeric forms of the groups in question. Thus, for example, propyloxy includes n-propyloxy and isopropyloxy, butyloxy includes isobutyloxy, sec-butyloxy, and tert-butyloxy, etc. The word alkoxy may also possibly be used within the scope of the present invention instead of the word alkyloxy. The groups methyloxy, ethyloxy, propyloxy, or butyloxy may optionally also be referred to as methoxy, ethoxy, propoxy, or butoxy.

The alkylene-alkyloxy groups used, unless otherwise stated, are branched and unbranched double-bonded alkyl bridges with 1 to 4 carbon atoms which may be mono-, di-, or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonyl carbon of the ester group. The term —O—CO-alkyl-halogen group should be understood analogously. The group —O—CO—$CF_3$ denotes trifluoroacetate.

Within the scope of the present invention, halogen denotes fluorine, chlorine, bromine, or iodine. Unless otherwise stated, fluorine and bromine are the preferred halogens. The group CO denotes a carbonyl group.

As explained hereinafter, the compounds according to the invention may be prepared partly analogously to the methods already known in the art (Diagram 1). The carboxylic acid derivatives of formula 3 are known in the art or may be obtained by methods of synthesis known in the art. If only suitably substituted carboxylic acids are known in the art, the compounds of formula 3 may also be obtained directly from them by acid- or base-catalyzed esterification with the corresponding alcohols or by halogenation with the corresponding halogenation reagents.

Diagram 1

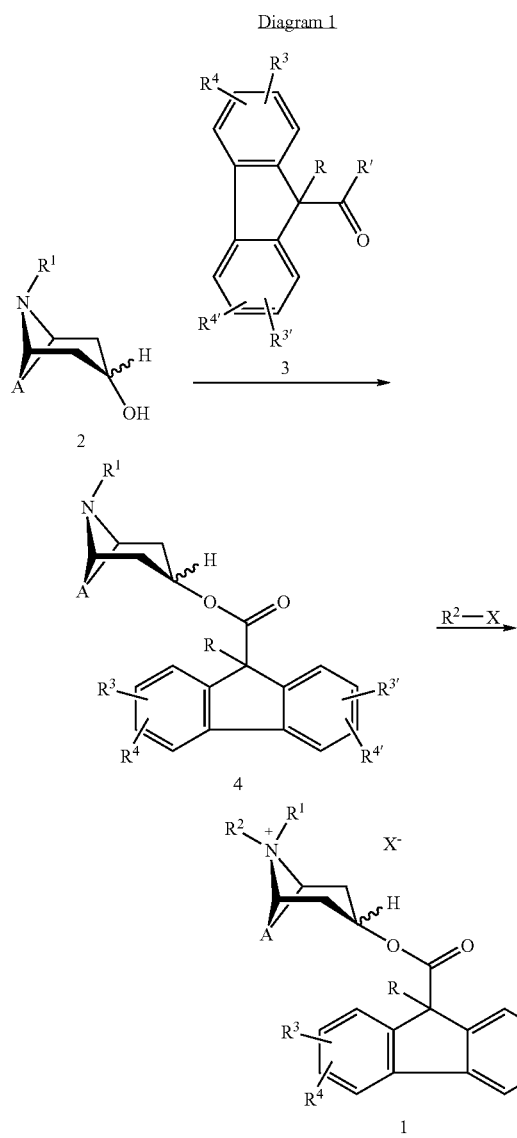

As can be seen from Diagram 1, the compounds of formula 2 may be used as starting products for preparing the compounds of formula 1. These compounds are known in the art.

Starting from the compounds of formula 2 the esters of general formula 4 may be obtained by reaction with the carboxylic acid derivatives of formula 3, wherein R' denotes, for example, chlorine or a $C_1$-$C_4$-alkyloxy group. When R' equals $C_1$-$C_4$-alkyloxy, this reaction may be carried out, for example, in a sodium melt at elevated temperature, preferably at about 50° C.-150° C., more preferably at about 90° C.-100° C. at low pressure, preferably at below 500 mbar, most preferably at below 75 mbar. Alternatively, instead of the derivatives 3 wherein R' denotes $C_1$-$C_4$-alkyloxy, the corresponding acid chlorides (R is Cl) may also be used.

The compounds of formula 4 thus obtained may be converted into the target compounds of formula 1 by reacting with the compounds $R^2$—X, wherein $R^2$ and X may have the abovementioned meanings. This synthesis step may also be carried out analogously to the examples of synthesis disclosed in WO 92/16528. In the case wherein $R^1$ and $R^2$ together form an alkylene bridge, there is no need to add the reagent $R^2$—X, as will be apparent to one of skill in the art. In this case, the compounds of formula 4 contain a suitably substituted group $R^1$ (for example, —$C_3$-$C_5$-alkylene-halogen) according to the above definitions and the compounds of formula 1 are prepared by intramolecular quaternization of the amine.

Alternatively to the method of synthesizing the compounds of formula 4 shown in Diagram 1, the derivatives 4, wherein the nitrogen bicyclic group denotes a scopine derivative, may be obtained by oxidizing (epoxidizing) compounds of formula 4 wherein the nitrogen bicyclic group is a tropenyl group. According to the invention, the following procedure may be used.

The compound 4 wherein A denotes —CH=CH— is suspended in a polar organic solvent, preferably in a solvent selected from among N-methyl-2-pyrrolidone (NMP), dimethylacetamide, and dimethylformamide, preferably dimethylformamide, and then heated to a temperature of about 30° C.-90° C., preferably 40° C.-70° C. Then a suitable oxidizing agent is added and the mixture is stirred at constant temperature for 2 to 8 hours, preferably 3 to 6 hours. The oxidizing agent is preferably vanadium pentoxide mixed with $H_2O_2$, most preferably $H_2O_2$-urea complex combined with vanadium pentoxide. The mixture is worked up in the usual way. The products may be purified by crystallization or chromatography depending on their tendency to crystallize.

Alternatively, the compounds of formula 4 wherein R denotes halogen may also be prepared by the method shown in Diagram 2.

Diagram 2

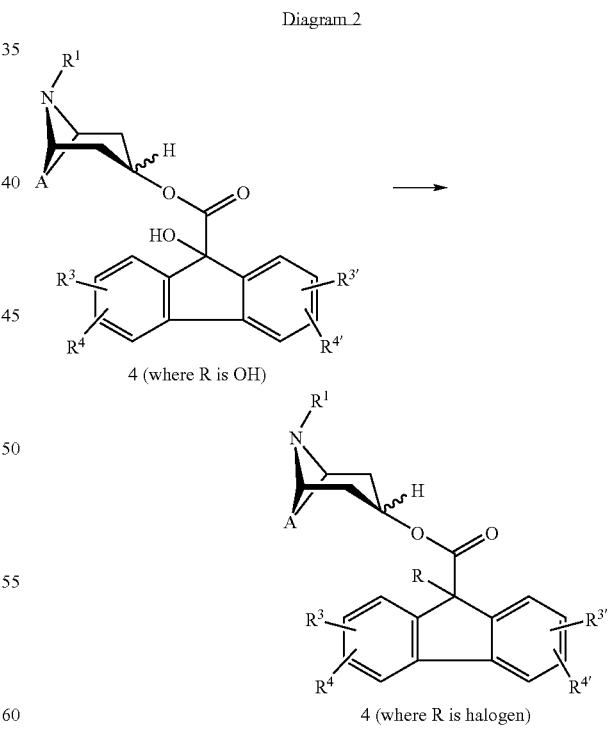

For this, the compounds of formula 4 wherein R denotes hydroxy are converted into the compounds 4 wherein R denotes halogen using suitable halogenation reagents. The method used for the halogenation reactions to be carried out according to Diagram 2 is sufficiently well known in the art.

As is apparent from Diagram 1, the intermediate products of general formula 4 have a central importance. Accordingly, in another aspect, the present invention relates to the intermediates of formula 4

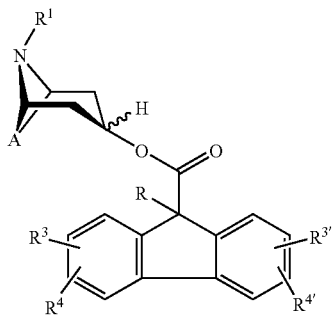

wherein the groups A, R, $R^1$, $R^3$, $R^{3'}$, $R^4$, and $R^{4'}$ may be defined as above, optionally in the form of the acid addition salts thereof.

By acid addition salts are meant salts selected from among the hydrochloride, hydrobromide, hydroiodide, hydrosulfate, hydrophosphate, hydromethanesulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate, preferably the hydrochloride, hydrobromide, hydrosulfate, hydrophosphate, hydrofumarate, and hydromethanesulfonate.

As in the compounds of general formula 1 the groups $R^3$, $R^4$, $R^{3'}$, and $R^{4'}$, if they do not represent hydrogen, may in each case be arranged in the ortho, meta, or para position relative to the bond of the "—C—R" group in the compounds of general formula 4 as well. If none of the groups $R^3$, $R^4$, $R^{3'}$, and $R^{4'}$ denotes hydrogen, $R^3$ and $R^{3'}$ are preferably linked in the para position and $R^4$ and $R^{4'}$ are preferably linked in the ortho or meta position, most preferably in the meta position. If one of the groups $R^3$ and $R^4$ and one of the groups $R^{3'}$ and $R^{4'}$ denotes hydrogen, the other group in each case is preferably linked in the meta or para position, most preferably in the para position. If none of the groups $R^3$, $R^4$, $R^{3'}$, and $R^{4'}$ denotes hydrogen, the compounds of general formula 4 which are particularly preferred according to the invention are those wherein the groups $R^3$, $R^4$, $R^{3'}$, and $R^{4'}$ have the same meaning.

According to the invention, the compounds of formula 4 in the α-configured form are preferably used as the starting materials. These α-configured compounds are therefore of particular importance according to the invention and correspond to general formula 4-α

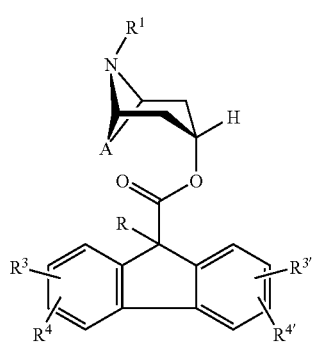

In another aspect, the present invention relates to the use of compounds of general formula 2 for preparing the compounds of general formula 4. Moreover, the present invention relates to the use of the compounds of general formula 2 as starting materials for preparing the compounds of general formula 1. Moreover, the present invention relates to the use of the compounds of general formula 4 as an intermediate product in the preparation of the compounds of general formula 1.

The examples of synthesis described below serves to illustrate the present invention still further. However, they are to be regarded as only an example of the procedure, as further illustration of the invention, without restricting the invention to the object described below by way of example.

EXAMPLE 1 tropenol 9-hydroxyfluorene-9-carboxylate methobromide

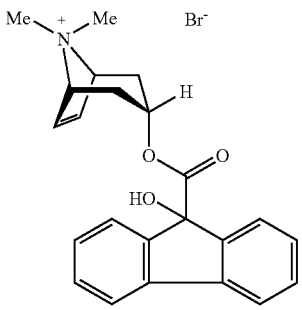

1.1.: methyl 9-hydroxyfluorene-9-carboxylate 3a 50.4 g (0.223 mol) of 9-hydroxy-9-fluorenecarboxylic acid are dissolved in 500 mL of methanol, combined with 5 mL (0.089 mol) of concentrated sulfuric acid and refluxed for 1 hour. After cooling, 100 mL of sodium hydrogen carbonate solution (about pH 8) are added and the methanol is largely evaporated down. The mixture is extracted with dichloromethane and water, the organic phase is dried and evaporated to dryness. The product is purified by recrystallization from ethyl acetate. Yield: 50.0 g of white crystals (93% of theoretical yield).

1.2: tropenol 9-hydroxyfluorene-9-carboxylate 4a 13.4 g (0.056 mol) of methyl ester 3a, 11.65 g (0.084 mol) of tropenol, and 0.3 g of sodium are heated as a melt at 75 mbar for 4 hours over a bath of boiling water with occasional agitation. After cooling, the sodium residues are dissolved with acetonitrile, the solution is evaporated to dryness, and the residue is extracted with dichloromethane/water. The organic phase is washed with water, dried over magnesium sulfate ($MgSO_4$), and the solvent is distilled off. The product is purified by recrystallization from diethyl ether. Yield: 11.40 g of white crystals (29% of theoretical yield).

1.3: tropenol 9-hydroxyfluorene-9-carboxylate methobromide 1.75 g (0.005 mol) of 4a are taken up in 30 mL dichloromethane and 15 mL acetonitrile and combined with 2.85 g (0.015 mol) of 50% methylbromide solution in acetonitrile. The reaction mixture is left to stand for 3 days at ambient temperature, during which time the product crystallizes. The crystals precipitated are separated off and recrystallized from diethyl ether to purify them. Yield: 1.95 g of white crystals (88% of theoretical yield); melting point: 250° C.; elemental analysis: calculated: C (62.45), H (5.47), N (3.17); found: C (61.53), H (5.84), N (3.22).

EXAMPLE 2 tropenol 9-fluorofluorene-9-carboxylate methobromide

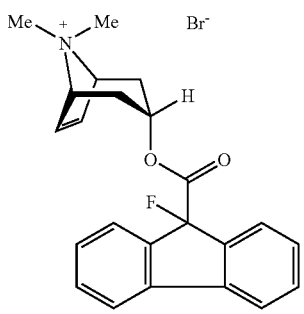

2.1: tropenol 9-fluorofluorene-9-carboxylate 4b 1.66 mL (0.009 mol) of bis-(2-methoxyethyl)aminosulfur trifluoride are placed in 10 mL dichloromethane and within 20 minutes at 15°-20° C., a solution of 2.4 g (0.007 mol) of 4a in 25 mL dichloromethane is added dropwise thereto. The mixture is stirred for 20 hours at ambient temperature, cooled to 0° C., and carefully combined with 80 mL of water with thorough stirring. Then the mixture is carefully adjusted to pH 8 with aqueous $NaHCO_3$ solution, the organic phase is separated off, the aqueous phase is extracted again with dichloromethane, the combined organic phases are washed with water, dried over magnesium sulfate, and evaporated to dryness. The hydrochloride is precipitated and recrystallized from acetonitrile-diethyl ether. Then the free base is liberated again using 10% aqueous sodium carbonate solution. Yield: 1.05 g bright yellow crystals (53% of theoretical yield).

2.2: tropenol 9-fluorofluorene-9-carboxylate Methobromide 1.05 g (0.003 mol) of 4b are taken up in 20 mL acetonitrile and reacted with 1.71 g (0.009 mol) of 50% methyl bromide solution in acetonitrile analogously to step 1.3. To purify it, the product is recrystallized from acetonitrile. Yield: 0.80 g of white crystals (60% of theoretical yield); melting point: 252° C.; elemental analysis: calculated: C (62.17), H (5.22), N (3.15); found: C (62.04), H (5.23), N (3.15).

EXAMPLE 3 scopine 9-hydroxyfluorene-9-carboxylate methobromide

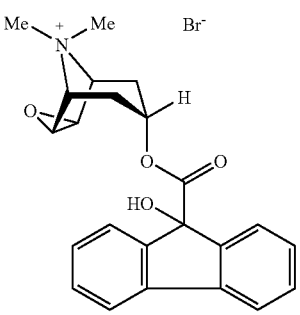

3.1: scopine 9-hydroxyfluorene-9-carboxylate 4c 9.0 g (0.026 mol) of tropenol ester 4a are suspended in 90 mL of dimethylformamide and combined with 0.47 g (0.003 mol) of vanadium (V) oxide. At 60° C., a solution of 4.89 g (0.052 mol) of $H_2O_2$-urea in 20 mL of water is added dropwise and stirred for 6 hours at 60° C. After cooling to 20° C., the precipitate formed is suction filtered, the filtrate is adjusted to pH 2 with 4 N hydrochloric acid and combined with $Na_2S_2O_5$ dissolved in water. The resulting solution is evaporated to dryness and the residue is extracted with dichloromethane-water. The acidic aqueous phase is made basic with $Na_2CO_3$, extracted with dichloromethane, and the organic phase is dried over $Na_2SO_4$ and concentrated. Then 1 mL of acetyl chloride is added at ambient temperature and the mixture is stirred for 1 hour. After extraction with 1 N hydrochloric acid, the aqueous phase is made basic, extracted with dichloromethane, the organic phase is washed with water and dried over $Na_2SO_4$. Then the solvent is removed by distillation. The crude product is purified by recrystallization from diethyl ether. Yield: 2.8 g of white crystals (30% of theoretical yield).

3.2: scopine 9-hydroxyfluorene-9-carboxylate methobromide 1.3 g (0.004 mol) 4c are taken up in 20 mL chloroform and 20 mL acetonitrile and reacted with 2.279 g (0.012 mol) of 50% methylbromide solution in acetonitrile analogously to step 1.3. To purify it, the product is recrystallized from acetonitrile. Yield: 1.25 g of light beige crystals (68% of theoretical yield); melting point: 243° C.-244° C.; elemental analysis: calculated: C (60.27), H (5.28), N (3.06); found: C (60.03), H (5.35), N (3.55).

EXAMPLE 4 scopine 9-fluorofluorene-9-carboxylate methobromide

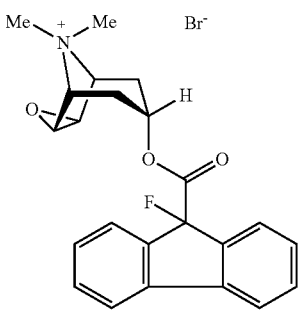

4.1: scopine 9-fluorofluorene-9-carboxylate 4d 0.885 mL (0.005 mol) of bis-(2-methoxyethyl)aminosulfur trifluoride are placed in 25 mL of dichloromethane and reacted with 1.42 g (0.004 mol) of 4c analogously to the procedure according to 2.1. Yield: 1.1 g beige crystals (75% of theoretical yield).

4.2: scopine 9-fluorofluorene-9-carboxylate methobromide 1.1 g (0.003 mol) of 4d are taken up in 30 mL acetonitrile and reacted with 1.71 g (0.009 mol) of 50% methyl bromide solution in acetonitrile analogously to step 1.3. To purify it, the product is recrystallized from isopropanol. Yield: 0.45 g of white crystals (33% of theoretical yield); melting point: 200° C.-201° C.; elemental analysis: calculated: C (60.01), H (5.04), N (3.04); found: C (59.91), H (5.18), N (3.10).

EXAMPLE 5 tropenol 9-methylfluorene-9-carboxylate methobromide

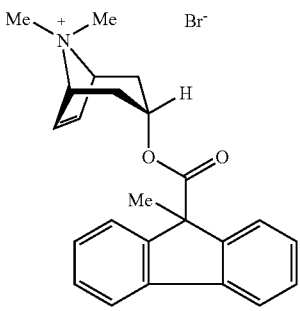

5.1.: 9-methylfluorene-9-carboxylic acid 3b a) methyl 9-methylfluorene-9-carboxylate From 7.6 g (0.33 mol) of sodium and 300 mL of ethanol, a sodium ethoxide solution is prepared, to which 69.6 g (0.33 mol) of 9-fluorenecarboxylic acid are added batchwise. After the addition has ended, the mixture is stirred for 2.5 hours at ambient temperature. Then it is evaporated to dryness, the residue is suspended in 600 mL of dimethylformamide, and 93.96 g (0.662 mol) of methyl iodide are added dropwise. The mixture is stirred for 3 hours at constant temperature. The cloudy solution is stirred into 500 mL of water and 300 mL of diethyl ether with cooling and extracted, the organic phase is washed with water and 10% sodium carbonate solution, dried, and evaporated to dryness. The residue is purified by column chromatography, eluent: cyclohexane-ethyl acetate (96:4). Yield: 12.61 g of white crystals (16% of theoretical yield); melting point: 108° C.-109° C.

b) 9-methylfluorene-9-carboxylic acid 3b:

12.6 g (0.053 mol) of methyl 9-methylfluorene-9-carboxylate and 53 mL of 2 molar, aqueous sodium hydroxide solution are stirred in 120 mL of 1,4-dioxane for 24 hours at ambient temperature. The dioxane is distilled off, made up to a total volume of 300 mL with water, and extracted with diethyl ether. The aqueous phase is acidified with 3 molar aqueous HCl, crystallized, and filtered. Yield: 11.25 g of white crystals (95% of theoretical yield); melting point: 168° C.-169° C.

5.2: tropenol 9-methylfluorene-9-carboxylate 4e:

6.73 g (0.03 mol) of 3b are suspended in 60 mL dichloromethane, combined with 5.0 g of oxalyl chloride and 1 drop of dimethylformamide, then stirred for one hour at ambient temperature and finally the solvent is distilled off. The acid chloride remaining is used in the next step without any further purification.

4.18 g (0.03 mol) of tropenol and 4.27 g (0.033 mol) of diisopropylethylamine are suspended in 100 mL of dichloroethane, the acid chloride is added dropwise to 30 mL of dichloroethane at 35° C.-40° C. and then stirred for 24 hours at 40° C. The suspension is diluted with dichloromethane and extracted with dilute hydrochloric acid. The organic phase is then washed with water, dried over magnesium sulfate and the product is converted into its hydrochloride with a solution of HCl in diethyl ether. The solvent is then removed. To purify it, the precipitated hydrochloride is taken up in water and extracted with diethyl ether. The aqueous phase is made basic with 10% aqueous sodium carbonate solution and extracted with dichloromethane. The organic phase is dried over magnesium sulfate and the solvent is distilled off. Yield: 4.40 g of yellow oil (42% of theoretical yield).

5.3: tropenol 9-methylfluorene-9-carboxylate methobromide 1.8 g (0.005 mol) of the free base 4e are reacted analogously to the method in step 1.3. The product is purified by recrystallization from acetone. Yield: 1.80 g of white crystals (82% of theoretical yield); melting point: 258° C.-259° C.; elemental analysis: calculated: C (65.46), H (5.95), N (3.18); found: C (64.15), H (5.95), N (3.18).

EXAMPLE 6 scopine 9-methylfluorene-9-carboxylate methobromide

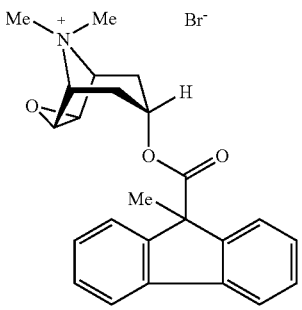

6.1: scopine 9-methylfluorene-9-carboxylate 4f 2.5 g (0.007 mol) of tropenol ester 4e are reacted with 0.13 g (0.001 mol) of vanadium (V) oxide and 1.43 g (0.015 mol) of $H_2O_2$-urea analogously to the process according to step 3.1. Yield: 1.8 g of white crystals (71% of theoretical yield).

6.2: scopine 9-methylfluorene-9-carboxylate methobromide 1.8 g (0.005 mol) of 4f are taken up in 30 mL acetonitrile and reacted with 2.848 g (0.015 mol) of 50% methyl bromide solution in acetonitrile analogously to step 1.3. Yield: 1.6 g of white crystals (70% of theoretical yield); melting point: 214° C.; elemental analysis: calculated: C (62.13), H (5.93), N (4.26); found: C (62.23), H (6.05), N (4.32).

It was found that the compounds according to the invention of formula 1 are antagonists of the M3 receptor (Muscarinic Receptor subtype 3). The compounds according to the invention have $K_i$ values of less than 10 nM in terms of their affinity for the M3 receptor. These values were determined by the method described below.

Chemicals $^3$H-NMS was obtained from Messrs Amersham of Braunschweig, with a specific radioactivity of 3071 GBq/mmol (83 Ci/mmol). All the other reagents were obtained from Serva of Heidelberg and Merck of Darmstadt.

Cell Membranes

We used cell membranes from CHO (Chinese hamster ovary) cells which were transfected with the corresponding genes of the human muscarinic receptor subtypes hm1 to hm5 (BONNER). The cell membranes of the desired subtype were thawed, resuspended by hand with a glass homogenizer, and diluted with HEPES buffer to a final concentration of 20-30 mg of protein/mL.

Receptor Binding Studies

The binding assay was carried out in a final volume of 1 mL and consisted of 100 μL of unlabelled substance in various concentrations, 100 μL of radioligand ($^3$H-N-methylscopolamine 2 nmol/L ($^3$H-NMS), 200 μL of membrane preparation, and 600 μL of HEPES buffer (20 mmol/L HEPES, 10 mmol/L $MgCl_2$, 100 mmol/L NaCl, adjusted with 1 mol/L NaOH to pH 7.4).

The nonspecific binding was determined using 10 μmol/L of atropine.

The preparation was incubated for 45 minutes at 37° C. in 96-well microtitre plates (Beckman, polystyrene, No. 267001) as a double measurement. The incubation was ended by filtering using an Inotech Cell Harvester (type IH 110) through Whatman G-7 filters. The filters were washed with 3 mL of ice-cooled HEPES buffer and dried before measuring.

Determining the Radioactivity

The radioactivity of the filter mats was measured simultaneously using a two-dimensional digital autoradiograph (Berthold, Wildbad, type 3052).

Evaluation

The $K_i$ values were calculated using implicit equations which were derived directly from the mass-action law, with the model for the 1 receptor 2 ligand reaction (SysFit—Software, SCHITTKOWSKI).

Literature

BONNER T I, *New Subtypes of Muscarinic Acetylcholine Receptors,* Trends Pharmacol. Sci. 10, Suppl.: 11-15 (1989); SCHITTKOWSKI K, *Parameter Estimation in Systems of Nonlinear Equations,* Numer Math. 68: 129-142 (1994).

The compounds of formula 1 according to the invention are characterized by their range of uses in the therapeutic field. Particular mention should be made of those applications for which the compounds of formula 1 according to the invention may preferably be used on the basis of their pharmaceutical activity as anticholinergics.

These are, for example, the treatment of asthma or COPD (chronic obstructive pulmonary disease). The compounds of general formula 1 may also be used to treat vagally induced sinus bradycardia and to treat heart rhythm disorders. Generally, the compounds according to the invention may also be used therapeutically to treat spasms, for example, in the gastrointestinal tract. They may also be used to treat spasms in the urinary tract and also to treat menstrual pain, for example. Of the ranges of indications mentioned above, the treatment of asthma and COPD with the compounds of formula 1 according to the invention is of particular importance.

The compounds of general formula 1 may be used on their own or in conjunction with other active substances of formula 1. The compounds of general formula 1 may also be used in combination with other pharmacologically active substances. These may be, in particular, betamimetics, antiallergics, PAF antagonists, PDE-IV inhibitors, leukotriene antagonists, p38 kinase inhibitors, EGFR-kinase inhibitors, and corticosteroids, as well as combinations of active substances.

Examples of betamimetics which may be used according to the invention in conjunction with the compounds of formula 1 include compounds selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo- 4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert-butylamino)ethanol and 1-(4-ethoxycarbonylamino-3-cyano-5-fluorophenyl)-2-(tert-butylamino)ethanol,
optionally in the form of the racemates, the enantiomers, the diastereomers and optionally the pharmacologically acceptable acid addition salts and the hydrates thereof. Most preferably, the betamimetics used as active substances in conjunction with the compounds of formula 1 according to the invention are selected from among fenoterol, formoterol, salmeterol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers, and optionally the pharmacologically acceptable acid addition salts thereof, and the hydrates thereof. Of the betamimetics mentioned above, the compounds formoterol and salmeterol are particularly preferred, optionally in the form of the racemates, the enantiomers, the diastereomers and optionally the pharmacologically acceptable acid addition salts thereof, and the hydrates thereof. According to the invention, the acid addition salts of the betamimetics selected, for example, from among the hydrochloride, hydrobromide, sulfate, phosphate, fumarate, methanesulfonate, and xinafoate are preferred. Particularly preferred in the case of salmeterol are the salts selected from among the hydrochloride, sulfate, and xinafoate, of which the xinafoate is particularly preferred. Particularly preferred in the case of formoterol are the salts selected from among the hydrochloride, sulfate, and fumarate, of which the hydrochloride and fumarate are particularly preferred. According to the invention, formoterol fumarate is of exceptional importance.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide, GW 215864, KSR 592, ST-126, and dexamethasone. Preferably, within the scope of the present invention, the corticosteroids are selected from among flunisolide, beclomethasone, triamcinolone, budesonide, fluticasone, mometasone, ciclesonide, and dexamethasone, while budesonide, fluticasone, mometasone and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A, and AWD-12-281. Preferred PDE-IV inhibitors are selected from among enprofylline, roflumilast, ariflo, and AWD-12-281, while AWD-12-281 is particularly preferred for combining with the compounds of general formula 1 according to the invention. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. According to the invention, the salts selected from among the acetate, hydrochloride, hydrobromide, sulfate, phosphate, and methanesulfonate are preferred.

Within the scope of the present invention, the term dopamine agonists, which may optionally be used in conjunction with the compounds of formula 1, denotes compounds selected from among bromocriptine, cabergolin, alpha-dihydroergocryptine, lisuride, pergolide, pramipexol, roxindole, ropinirole, talipexole, terguride, and viozan. It is preferable within the scope of the present invention to use, as combination partners with the compounds of formula 1, dopamine agonists selected from among pramipexol, talipexole, and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compound of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratadine, and mizolastine, epinastine and desloratadine being particularly preferred. Any reference to the abovementioned antiallergic agents also includes, within the scope of the present invention, a reference to any pharmacologically acceptable acid addition salts thereof which may exist.

Examples of PAF antagonists which may be used according to the invention as a combination with the compounds of formula 1 include 4-(2-chlorophenyl)-9-methyl-2-[3 (4-morpholinyl)-3-propanon-1-yl]-6H-thieno-[3,2-f][1,2,4]triazolo[4,3-a][1,4]diazepine and 6-(2-chlorophenyl)-8,9-dihydro-1-methyl-8-[(4-morpholinyl)carbonyl]-4H,7H-cyclopenta-[4,5]thieno-[3,2-f][1,2,4]triazolo[4,3-a][1,4]diazepine.

Especially preferred examples of EGFR-kinase inhibitors which may be used according to the invention as a combination with the compounds of formula 1 include, in particular, 4-[(3-chloro-4-fluorophenyl)amino]-7-[4-((R)-6-methyl-2- oxomorpholin-4-yl)butyloxy]-6-[(vinylcarbonyl)amino] quinazoline, 4-[(3-chloro-4-fluorophenyl)amino]-7-[4-((S)-6-methyl-2-oxomorpholin-4-yl)butyloxy]-6-[(vinylcarbonyl)amino]quinazoline, 4-[(3-chloro-4-fluorophenyl)amino]-7-(2-{4-[(S)-(2-oxotetrahydrofuran-5-yl)carbonyl]piperazin-1-yl}ethoxy)-6-[(vinylcarbonyl) amino]quinazoline, 4-[(3-chloro-4-fluorophenyl)amino]-7-[2-((S)-6-methyl-2-oxomorpholin-4-yl)ethoxy]-6-[(vinylcarbonyl)amino]quinazoline, 4-[(3-chloro-4-fluorophenyl)amino]-6-[(4-{N-[2-(ethoxycarbonyl)ethyl]-N-[(ethoxycarbonyl)methyl]amino}-1-oxo-2-buten-1-yl) amino]-7-cyclopropylmethoxyquinazoline, 4-[(R)-(1-phenylethyl)amino]-6-{[4-(morpholin-4-yl)-1-oxo-2-buten-1-yl]amino}-7-cyclopropylmethoxyquinazoline, and 4-[(3-chloro-4-fluorophenyl)amino]-6-[3-(morpholin-4-yl) propyloxy]-7-methoxyquinazoline. Any reference to the abovementioned EGFR-kinase inhibitors also includes, within the scope of the present invention, a reference to any pharmacologically acceptable acid addition salts thereof which may exist. By the physiologically or pharmacologically acceptable acid addition salts thereof which may be formed by the EGFR-kinase inhibitors are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. According to the invention the salts of the EGFR-kinase inhibitors selected from among the salts of acetic acid, hydrochloric acid, hydrobromic acid, sulfuric acid, phosphoric acid and methanesulfonic acid are preferred.

Particularly preferred examples of p38 kinase inhibitors which may be used according to the invention as a combination with the compounds of formula 1 include, in particular, 1-[5-tert-butyl-2-p-tolyl-2H-pyrazol-3-yl]-3-[4-(2-morpholin-4-ylethoxy)naphthalin-1-yl]urea; 1-[5-tert-butyl-2-p-tolyl-2H-pyrazol-3-yl]-3-[4-(2-(1-oxothiomorpholin-4-yl) ethoxy)naphthalin-1-yl]urea; 1-[5-tert-butyl-2-(2-methylpyridin-5-yl)-2H-pyrazol-3-yl]-3-[4-(2-pyridine-4-ylethoxy)naphthalin-1-yl]urea; 1-[5-tert-butyl-2-(2-methoxypyridin-5-yl)-2H-pyrazol-3-yl]-3-[4-(2-morpholin-4-ylethoxy)naphthalin-1-yl]urea, or 1-[5-tert-butyl-2-methyl-2H-pyrazol-3-yl]-3-[4-(2-morpholin-4-ylethoxy) naphthalen-1-yl]urea. Any reference to the abovementioned p38-kinase inhibitors also includes, within the scope of the present invention, a reference to any pharmacologically acceptable acid addition salts thereof which may exist. By the physiologically or pharmacologically acceptable acid addition salts thereof which may be formed by the p38 kinase inhibitors are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

If the compounds of formula 1 are used in conjunction with other active substances, the combination with steroids, PDE-IV inhibitors, or betamimetics is particularly preferred, of the categories of compounds mentioned above. The combination with betamimetics, particularly with long-acting betamimetics, is of particular importance. The combination of the compounds of formula 1 according to the invention with salmeterol or formoterol is particularly preferred.

Suitable preparations for administering the salts of formula 1 include, for example, tablets, capsules, suppositories, and solutions, etc. Administration of the compounds according to the invention by inhalation is of particular importance according to the invention (particularly for treating asthma or COPD). The content of the pharmaceutically active compound(s) should be in the range from 0.05 to 90 wt.-%, preferably 0. 1 to 50 wt.-% of the composition as a whole. Suitable tablets may be obtained, for example, by mixing the active substance(s) with known excipients, for example, inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide or sugar. To achieve delayed release or prevent incompatibilities, the core may also consist of a number of layers. Similarly, the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, and chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

For oral use the tablets may obviously contain, in addition to the carriers specified, additives such as sodium citrate, calcium carbonate and dicalcium phosphate together with various additional substances such as starch, preferably potato starch, gelatin, and the like. Lubricants such as magnesium stearate, sodium lauryl sulfate, and talc may also be used to produce the tablets. In the case of aqueous suspensions, the active substances may be combined with various flavor enhancers or colorings in addition to the abovementioned excipients.

When the compounds of formula 1 are used for the treatment of asthma or COPD they are preferably administered as preparations or pharmaceutical formulations for inhalation. For inhalation, the compounds may be in the form of inhalable powders, propellant-containing metering aerosols, or propellant-free inhalable solutions. Within the scope of the present invention, the term propellant-free inhalable solutions also includes concentrates or sterile inhalable solutions ready for use. The formulations which may be used within the scope of the present invention are described in detail in the next part of the specification.

The inhalable powders which may be used according to the invention may contain the compounds 1 either on their own or in admixture with suitable physiologically acceptable excipients. If the active substances 1 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, or maltose), oligo- and polysaccharides (e.g., dextrane), polyalcohols (e.g., sorbitol, mannitol, or xylitol), salts (e.g., sodium chloride or calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention, the excipients have a maximum average particle size of up to 250 µm, preferably between 10 µm and 150 µm, most preferably between 15 µm and 80 µm. It may sometimes seem appropriate to add finer excipient fractions with an average particle size of 1 µm to 9 µm to the excipients mentioned above. These finer excipients are also selected from the group of possible excipients listed hereinbefore. Finally, in order to prepare the inhalable powders according to the invention, micronised active substance 1, preferably with an average particle size of 0.5 µm to 10 µm, more preferably from 1 µm to 5 µm, is added to the excipient mixture. Processes for producing the inhalable powders according to the invention by grinding and micronizing and by finally mixing the ingredients together are known from the prior art. The inhalable powders according to the invention may be administered using inhalers known from the prior art.

The inhalation aerosols containing propellant gas which may be used according to the invention may contain the compounds 1 dissolved in the propellant gas or in dispersed form. The compounds 1 may be present in separate preparations or in a combined preparation, while the compounds 1 may either both be dissolved, both dispersed or only one component is dissolved and the other may be dispersed.

The propellant gases which may be used to prepare the inhalation aerosols are known from the prior art. Suitable propellant gases are selected from among hydrocarbons such as n-propane, n-butane, or isobutane, and halohydrocarbons such as fluorinated derivatives of methane, ethane, propane, butane, cyclopropane, or cyclobutane. The propellant gases mentioned above may be used on their own or in mixtures thereof. Particularly preferred propellant gases are fluorinated alkane derivatives selected from TG134a and TG227 and mixtures thereof.

The propellant-driven inhalation aerosols may also contain other ingredients such as cosolvents, stabilizers, surfactants, antioxidants, lubricants and pH adjusters. All these ingredients are known in the art.

The propellant-driven inhalation aerosols mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume, and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid. Preferred inorganic acids are hydrochloric and sulfuric acids. It is also possible to use the acids which already form an acid addition salt. Of the organic acids, ascorbic acid, fumaric acid and citric acid are preferred. If desired, mixtures of the above acids may be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

In these formulations it may be possible to do without the addition of edetic acid (EDTA) or one of the known salts thereof, sodium edetate, as stabilizer or complexing agent. Other embodiments contain these compounds. In a preferred embodiment, the content, based on sodium edetate, is less than 100 mg/100 mL, preferably less than 50 mg/100 mL, most preferably less than 20 mg/100 mL. Generally, inhalable solutions in which the content of sodium edetate is from 0 to 10 mg/100 mL are preferred. Cosolvents and/or other excipients may be added to the propellant-free inhalable solutions. Preferred cosolvents are those which contain hydroxyl groups or other polar groups, such as alcohols, particularly isopropyl alcohol, glycols, particularly propyleneglycol, polyethyleneglycol, polypropyleneglycol, glycol ether, glycerol, polyoxyethylene alcohols, and polyoxyethylene fatty acid esters. By excipients and additives are meant, in this context, any pharmacologically acceptable substance which is not an active substance, but can be formulated together with the active substance(s) in the pharmacologically suitable solvent to improve the qualitative properties of the active substance formulation. Preferably, these substances have no noticeable or at least no unwanted pharmacological activity in the context of the desired therapy. The excipients and additives include, e.g., surfactants such as soya lecithin, oleic acid, sorbitan esters such as polysorbates, polyvinylpyrrolidone, other stabilizers, complexing agents, antioxidants, and/or preservatives which guarantee or extend the shelf life of the finished pharmaceutical formulation, flavorings, vitamins and/or other additives known in the art. The additives also include pharmacologically acceptable salts such as for example sodium chloride as isotonic agents.

The preferred excipients include antioxidants, such as, for example, ascorbic acid, unless already used to adjust the pH, vitamin A, vitamin E, tocopherols, and similar vitamins or provitamins which occur in the human body.

Preservatives may be used to protect the formulation from contamination with pathogens. Suitable preservatives are those known in the art, particularly cetylpyridinium chloride, benzalkonium chloride, or benzoic acid or benzoates such as sodium benzoate in the concentration known from the prior art. The abovementioned preservatives are preferably present in concentrations of up to 50 mg/100 mL, most preferably between 5 and 20 mg/100 mL.

Preferred formulations contain only benzalkonium chloride and sodium edetate, in addition to the solvent water and the active substance 1. In another preferred embodiment, no sodium edetate is used.

The dosage of the compounds according to the invention is naturally highly dependent on the method of administration and the complaint which is being treated. When administered by inhalation the compounds of formula 1 are characterized by a high potency even at doses in the μg range. The compounds of formula 1 may also be used effectively above the μg range. The dosage may then be in the gram range, for example.

When administered by routes other than by inhalation the compounds according to the invention may be administered in higher doses (for example, but not restrictively, in the range from 1 to 1000 mg).

The following examples of formulations illustrate the present invention without restricting its scope:

EXAMPLES OF PHARMACEUTICAL FORMULATIONS

A. Tablets Containing 100 mg of Active Substance

| Component | Amount per tablet (mg) |
| --- | --- |
| active substance 1 | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated, and dried. The granules, the remaining corn starch and the magnesium stearate are screened and mixed together. The mixture is compressed to produce tablets of suitable shape and size.

B. Tablets Containing 80 mg of Active Substance

| Component | Amount per tablet (mg) |
| --- | --- |
| active substance 1 | 80 |
| lactose | 55 |
| corn starch | 190 |
| microcrystalline cellulose | 35 |
| polyvinylpyrrolidone | 15 |
| sodium-carboxymethyl starch | 23 |
| magnesium stearate | 2 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

C. Ampoule Solution Containing 50 mg of Active Substance

| Component | Amount |
| --- | --- |
| active substance 1 | 50.0 mg |
| sodium chloride | 50 mg |
| water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg, and 50 mg of active substance.

D. Metering Aerosol

| Component | Amount |
| --- | --- |
| active substance 1 | 0.005 |
| sorbitan trioleate | 0.1 |
| monofluorotrichloromethane and difluorodichloromethane (2:3) | to 100 |

The suspension is transferred into a conventional aerosol container with metering valve. Preferably 50 μL suspension are released on each actuation. The active substance may also be released in higher doses if desired (e.g., 0.02 wt.-%).

E. Solution

| Component | mg/100 mL |
| --- | --- |
| active substance 1 | 333.3 |
| formoterol fumarate | 333.3 |
| benzalkonium chloride | 10.0 |
| EDTA | 50.0 |
| HCl (1N) | to pH 3.4 |

This solution may be prepared in the usual way.

F. Inhalable Powder

| Component | Amount |
| --- | --- |
| active substance 1 | 6 μg |
| formoterol fumarate | 6 μg |
| lactose monohydrate | to 25 mg |

The inhalable powder is prepared in the usual way by mixing the individual ingredients.

| G. Inhalable Powder | |
|---|---|
| Component | Amount |
| active substance 1 | 10 μg |
| lactose monohydrate | to 25 mg |

The inhalable powder is prepared in the usual way by mixing the individual ingredients.

What is claimed is:

1. Propellent-free inhalable solution or suspension containing the
   i) active substance according to formula 1 wherein

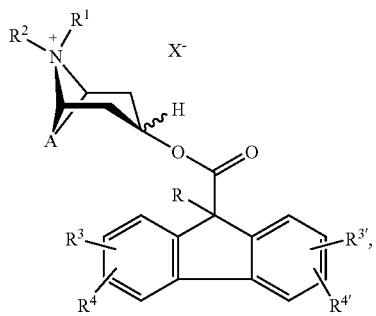

A denotes a double-bonded group selected from among

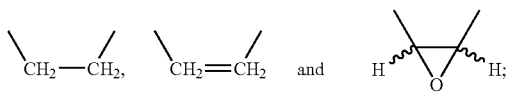

X- denotes an anion with a single negative charge,
R denotes hydrogen, hydroxy, methyl, ethyl, —$CF_3$, $CHF_2$ or fluorine;
$R^1$ and $R^2$ which may be identical or different denotes $C_1$-$C_5$-alkyl which may optionally be substituted by $C_3$-$C_6$-cycloalkyl, hydroxyl or halogen, or
$R^1$ and $R^2$ together denote a $C_3$-$C_5$-alkylene-bridge; and
$R^3$, $R^4$, $R^{3'}$ and $R^{4'}$ which may be identical or different denote hydrogen, $C_1$-$C_4$-alkyl, $C_1$-$C_4$-alkyloxy, hydroxy, —$CF_3$, —$CHF_2$, CN, $NO_2$ or halogen,
   ii) an aqueous or alcoholic solvent, or a mixture of water and ethanol and
   iii) an inorganic or organic acid.

2. Propellent-free inhalable solution or suspension according to claim 1, which has a pH of 2 to 7.

3. Propellent-free inhalable solution or suspension according to claim 1, which has a pH of 2 to 5.

4. Propellent-free inhalable solution or suspension according to claim 1, wherein the solvent is ethanol.

5. Propellent-free inhalable solution or suspension according to claim 1, wherein the solvent is water.

6. Propellent-free inhalable solution or suspension according to claim 1, wherein the solvent is a mixture of water and ethanol.

7. Propellent-free inhalable solution or suspension according to claim 1, wherein the inorganic acid is selected from the group consisting of hydrochloric acid, hydrobromic acid, nitric acid, sulphuric acid and phosphoric acid or wherein the organic acid is selected from the group consisting of ascorbic acid, citric acid, malic acid, tartaric acid, maleic acid, succinic acid, fumaric acid, acetic acid, formic acid and propionic acid.

8. Propellent-free inhalable solution or suspension according to claim 1, which additionally contains editic acid (EDTA) or one of the known salts thereof, as a stabiliser or complexing agent.

9. Propellent-free inhalable solution or suspension according to claim 1, which additionally contains a cosolvent, excipient or additive.

10. Propellent-free inhalable solution or suspension according to claim 1, wherein in the active substance according to formula 1
    X- denotes an anion with a single negative charge selected from among chloride, bromide, 4-toluenesulphonate and methanesulphonate;
    R denotes hydroxy, methyl or fluorine;
    $R^1$ and $R^2$ which may be identical or different denote methyl, ethyl or fluoroethyl; and
    $R^3$, $R^4$, $R^{3'}$ and $R^{4'}$ which may be identical or different represent hydrogen, methyl, methyloxy, hydroxy, —$CF_3$, —$CHF_2$ or fluorine.

11. Propellent-free inhalable solution or suspension according to claim 1, wherein in the active substance according to formula 1
    A denotes a double-bonded group selected from among

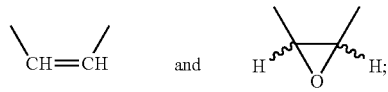

X- denotes an anion with a single negative charge selected from among chloride, bromide and methanesulphonate;
    R denotes hydroxy, methyl or fluorine;
    $R^1$ and $R^2$ which may be identical or different denote methyl or ethyl; and
    $R^3$, $R^4$, $R^{3'}$ and $R^{4'}$ which may be identical or different represent hydrogen, —$CF_3$, —$CHF_2$ or fluorine.

12. Propellent-free inhalable solution or suspension according to claim 1, wherein in the active substance according to formula 1
    A denotes a double-bonded group selected from among

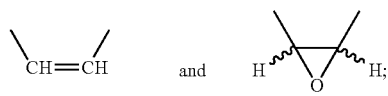

X- denotes bromide;
    R denotes hydroxy or methyl;
    $R^1$ and $R^2$ which may be identical or different denote methyl or ethyl; and
    $R^3$, $R^4$, $R^{3'}$ and $R^{4'}$ which may be identical or different represent hydrogen or fluorine.

13. Propellent-free inhalable solution or suspension according to claim 1, wherein the active substance according to formula 1

A denotes

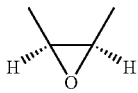

X- denotes bromide;

R denotes methyl;

$R^1$ and $R^2$ denotes methyl; and $R^3$, $R^4$, $R^{3'}$ and $R^{4'}$ denote hydrogen.

14. Propellent-free inhalable solution or suspension according to claim 1, which additionally contains sodium edetate as a stabiliser or complexing agent.

15. Propellent-free inhalable solution or suspension according to claim 9, wherein the cosolvent, excipient or additive is selected from the group consisting of surfactants, sorbitan esters, other stabilizers, complexing agents, antioxidants, preservatives, flavourings and vitamins.

16. Propellent-free inhalable solution or suspension according to claim 10, wherein in the active substance according to formula 1

X- denotes a bromide ion.

17. Propellent-free inhalable solution or suspension according to claim 11, wherein in the active substance according to formula 1

X- denotes a bromide anion;

R denotes methyl or hydroxy;

$R^1$ and $R^2$ denote methyl; and $R^3$, $R^4$, $R^{3'}$ and $R^{4'}$ which may be identical or different represent hydrogen, or fluorine.

18. Propellent-free inhalable solution or suspension according to claim 12, wherein in the active substance according to formula 1

R denotes methyl; and $R^1$ and $R^2$ denote methyl.

19. Propellent-free inhalable solution or suspension according to claim 1, wherein in the active substance according to formula 1

A denotes a double-bonded group selected from among

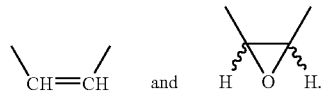

20. Propellent-free inhalable solution or suspension according to claim 1, wherein in the active substance according to formula 1

R denotes hydrogen, hydroxy, methyl, ethyl, —$CF_3$, $CHF_2$ fluorine.

* * * * *